(12) United States Patent
Klee et al.

(10) Patent No.: US 8,372,896 B2
(45) Date of Patent: Feb. 12, 2013

(54) TOTAL ETCH DENTAL ADHESIVE COMPOSITION

(75) Inventors: Joachim E. Klee, Radolfzell (DE); Uwe Lehmann, Konstanz (DE); Franziska Heinzmann, Mönchweiler (DE)

(73) Assignee: DENTSPLY International Inc., York, PA (US)

( * ) Notice: Subject to any disclaimer, the term of this patent is extended or adjusted under 35 U.S.C. 154(b) by 44 days.

(21) Appl. No.: 12/319,949

(22) Filed: Jan. 13, 2009

(65) Prior Publication Data
US 2010/0179244 A1    Jul. 15, 2010

(51) Int. Cl.
*A61K 6/00* (2006.01)
*A61K 6/083* (2006.01)
*A61F 2/00* (2006.01)
*A61L 24/00* (2006.01)

(52) U.S. Cl. ......... 523/118; 523/113; 523/115; 523/116
(58) Field of Classification Search ................... 523/118
See application file for complete search history.

(56) References Cited

U.S. PATENT DOCUMENTS
2002/0143138 A1* 10/2002 Moszner et al. ............. 528/310

FOREIGN PATENT DOCUMENTS
| EP | 1548021 A1 * | 6/2005 |
| EP | 1674067 B1 | 4/2009 |
| WO | WO 03/013444 | 2/2003 |
| WO | WO 03/035013 | 5/2003 |

* cited by examiner

*Primary Examiner* — Peter F Godenschwager
*Assistant Examiner* — David Karst
(74) *Attorney, Agent, or Firm* — David A. Zdurne; Douglas J. Hura; Leana Levin

(57) ABSTRACT

Dental adhesive composition having a pH of at least 5, which comprises an aqueous solution containing
  (a) a polymerizable N-substituted alkyl acrylic or acrylic acid amide monomer;
  (b) a water-soluble polymerizable carboxylic acid; and
  (c) a water-soluble organic solvent.

23 Claims, 3 Drawing Sheets

TOTAL ETCH DENTAL ADHESIVE COMPOSITION

FIELD OF THE INVENTION

The present invention relates to a dental adhesive. In particular, the present invention relates to a dental adhesive for use in a total-etch adhesive bonding technique for sealants, orthodontic brackets, anterior composite resins, posterior composite resins, bonded dental silver amalgam, resin cementation with posts, all-metal, porcelain-metal, composite resin, and ceramic restorations, splinting, core foundations, and conservative treatment of a worn dentition.

BACKGROUND TO THE INVENTION

The concept of total etch adhesion for enamel and dentin is known. The total etch technique relates to the simultaneous etching of enamel and dentin using a phosphoric acid gel in order to remove a smear layer and to make microporosities accessible for a subsequently applied dental adhesive composition. The acid is completely removed by subsequent air-water jet spray washing. The tubule apertures are sealed by the protective bonding agent layer with resin tags adhering to the tubule walls and the resin-impregnated dentin surface.

However, the total etch technique is problematic in that excessive drying of the etched tooth surface (especially dentin) may lead to inferior bonding properties. In order to avoid a separate etching step and the problems associated with subsequent acid removal and drying, self etching compositions were proposed. Self etching composition typically have an acidic pH of less than 2 and are capable of passing the smear layer. However, the self etching technique gives rise to further problems even when a self cure activator is used for curing. The dental cement is frequently inactivated at the interface to the dental adhesive so that bonding and curing cannot proceed efficiently.

It is the problem of the present invention to provide a dental adhesive composition for use in a total-etch adhesive bonding technique wherein the problems associated with excessive drying are avoided and wherein an improved adhesion in terms of shear bond strength to dentin and enamel is provided at a level of at least 15 MPa, and whereby the adhesion to enamel and the adhesion to dentin in terms of the shear bond strength are of similar magnitude.

DISCLOSURE OF THE INVENTION

The present invention provides a dental adhesive composition having a pH of at least 5, which comprises an aqueous solution containing
  (a) a polymerizable N-substituted alkyl acrylic or acrylic acid amide monomer;
  (b) a water-soluble polymerizable carboxylic acid; and
  (c) a water-soluble organic solvent.

The present invention is based on the recognition that an extremely strong bonding may be provided based on an aqueous solution capable of adjusting the moisture of the tooth surface provided that the composition contains components which are efficiently wetting the surface of the tooth at a pH of at least 5 for forming a polymerizable film. Given the presence of water in the composition, the presence of ester bonds in the composition which might hydrolyse during storage should be avoided.

DISCLOSURE OF THE PREFERRED EMBODIMENTS

Figure 1:
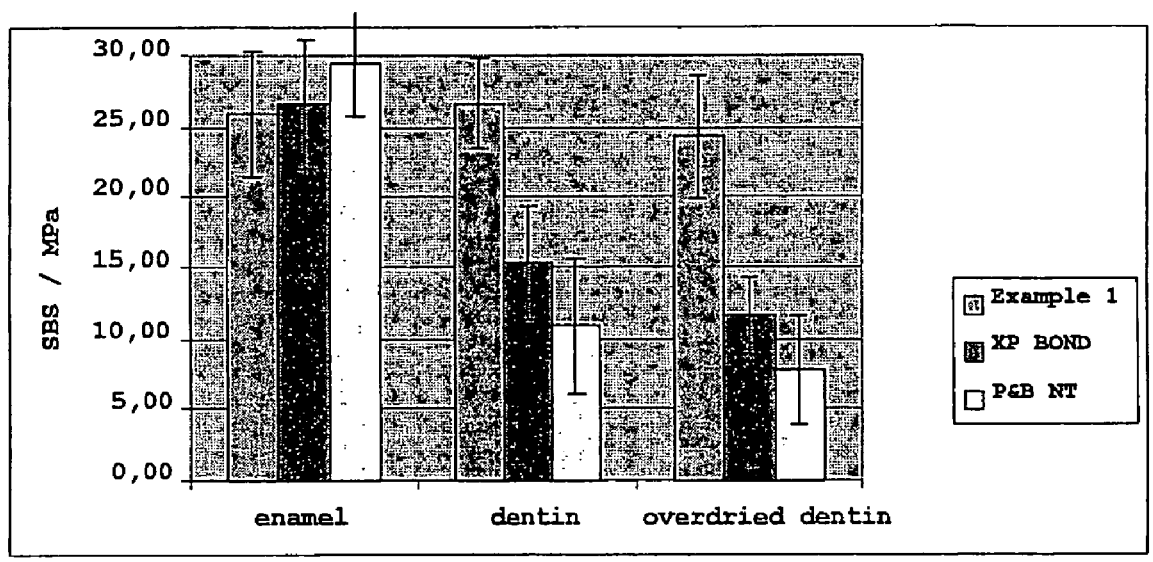
FIG. 1 shows the adhesion between a composition according to Example 1 and a light curing composite (Spectrum TPH) in comparison to XP Bond and Prime&Bond NT in total etch technique, polymerized with a Spectrum 800 curing unit, whereby the storage conditions prior to shear bond strength measurement were storage for 24 h at 37° C. and thermocyling between 5 to 55° C. for 1800 times.

The dental adhesive composition according to the invention comprises an aqueous solution. The aqueous solution provides moisture for the tooth structure in case of excessive drying of the tooth surface in the total etch technique.

The aqueous solution contains an aqueous medium, polymerizable components and optionally an initiator, stabilizer and/or inhibitor. The dental adhesive composition has a pH of at least 5, preferably in the range of from 5 to 9.

The aqueous medium comprises water and optionally one or more water miscible organic solvents. Preferably, water is present in an amount of from 5 to 45 wt. % based on the dental adhesive composition. More preferably, water is present in an amount of from 20 to 40 wt. % based on the dental adhesive composition. If the water content is below 5 wt. %, then the dental adhesive might not be effective in moisturizing the tooth surface when the surface has been excessively dried.

The water-soluble organic solvent may be selected from alcohols and ketones. Specifically, the water-soluble organic solvent may be selected from ethanol, n-propanol, i-propanol, n-butanol, t-butanol, acetone, and methyl ethyl ketone. t-Butanol is particularly preferred. The water-soluble organic solvent may be present in an amount of from 5 to 45 wt. % based on the dental adhesive composition. More preferably, the water-soluble organic solvent may be present in an amount of from 8 to 30 wt. %.

The polymerizable components comprise a polymerizable N-substituted alkyl acrylic or acrylic acid amide monomer which may be preferably selected from compounds characterized by one of the following formulas:

The polymerizable components comprise a polymerizable N-substituted alkyl acrylic or acrylic acid amide monomer which may be preferably selected from compounds characterized by one of the following formulas:

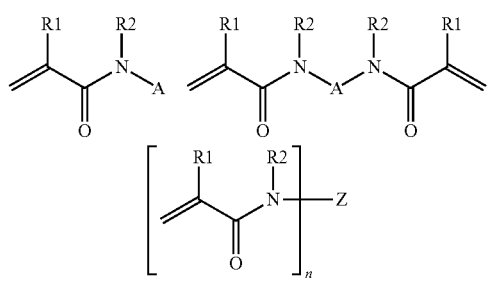

wherein $R_1$ and $R_2$ independently represent a hydrogen atom or a $C_1$ to $C_8$ alkyl group; A represents a divalent substituted or unsubstituted organic residue having from 1 to 11 carbon atoms, whereby said organic residue may contain from 1 to 3 oxygen and/or nitrogen atoms; Z represents a saturated at least trivalent substituted or unsubstituted $C_1$ to $C_6$ hydrocarbon group, a saturated at least trivalent substituted or unsubstituted cyclic $C_3$ to $C_8$ hydrocarbon group, and n is at least 3.

Preferably, the polymerizable monomer may be a mono-, bis- or poly(meth) acrylamide characterized by the following formula:

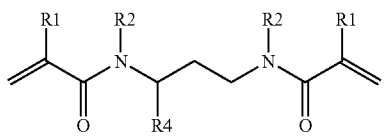

wherein $R_1$, $R_2$ and $R_4$ independently represent a hydrogen atom or a $C_1$ to $C_8$ alkyl group. Preferably, 1,3-Bisacrylamido propane (BAP) or 1,3-Bisacrylamido. pentane (BAPEN) may be used.

The polymerizable water soluble N-substituted alkyl acrylic or acrylic acid amide monomer may be present in an amount of 20 to 60 wt. %, more preferably 30 to 50 wt. %, based on the dental adhesive composition.

Preferably, the polymerizable N-substituted alkyl acrylic or acrylic acid amide monomer has a molecular weight of at most 400, more preferably at most 300.

The polymerizable components also comprise a the water-soluble polymerizable carboxylic acid which may be selected from the group of mono- or polycarboxylic acids. Specifically, the mono- or polycarboxylic acids are selected from the group of acrylic acid, methacrylic acid, fumaric acid, maleic acid, itaconic acid, and mixtures thereof. The water-soluble organic acid may be present in an amount of from 3 to 20 wt. %, more preferably 5 to 15 wt. %, based on the dental adhesive composition.

Preferably, the water-soluble polymerizable carboxylic acid has a molecular weight of at most 400, more preferably at most 300.

Preferably, the polymerizable water soluble N-substituted alkyl acrylic or acrylic acid amide monomer and the water-soluble polymerizable carboxylic acid are contained in a ratio of from 7:1 to 1:1, preferably, 5:1 to 1:1 by weight.

The dental adhesive composition according to the present invention may further comprise a polymerization initiator, inhibitor and/or stabilizer. The polymerization initiator may be a thermal initiator, a redox-initiator or a photo initiator. The photo initiator may be camphor quinine/amine and/or an acylphosphine oxide. The inhibitor and/or stabilizer may be selected from hydroquinone, hydroquinone monomethyl ether, ditert. butyl cresol, tert. butyl hydroquinone.

In a specific embodiment, the dental adhesive composition may further comprise a nanofiller having an average particle size in the range of from 1 to 100 nm, preferably 1 to 10 nm.

In a specific embodiment, the dental adhesive composition may further comprise a fluoride containing compound.

In a preferred embodiment, the dental adhesive composition consists essentially of an aqueous solution containing
  (a) a polymerizable N-substituted alkyl acrylic or acrylic acid amide monomer;
  (b) a water-soluble polymerizable carboxylic acid; and
  (c) a water-soluble organic solvent
and optionally a filler, fluoride containing compound, initiator, stabilizer and/or inhibitor.

Preferably, the dental adhesive composition provides adhesion. in terms of shear bond strength to dentin and enamel at a level of at least 15 MPa, whereby the adhesion to dentin in terms of the shear bond strength is at least 50%, more preferably at least 70% of the adhesion to enamel in terms of the shear bond strength.

The invention will now be illustrated with reference to the following non-limiting examples

EXAMPLES

Example 1

The following dental adhesive composition was prepared. The composition had a pH of 5.5.

| Components/wt. % | Example 1 |
| --- | --- |
| Water | 28.800 |
| 1,3-Bisacrylamido propane | 23.047 |
| 1,3-Bisacrylamido pentane | 23.048 |
| Acrylic acid | 9.000 |
| t-Butanol | 12.713 |
| tert. Butyl hydroquinone | 0.051 |
| camphor quinone | 0.714 |
| Acylphosphin oxide (L-TPO Lucirin) | 1.796 |
| 4-Dimethylamino benzonitrile | 0.830 |
| TOTAL | 100 |

The mixture is a clear solution of low viscosity suitable for use in a total etch procedure. The composition provides excellent wetting properties of the tooth surface even when the tooth surface was overdried. Due to the absence of ester bonds, the storage stability of the composition is excellent.

Example 2

Direct Restoration

The composition according to Example 1 was applied to a dental surface and light cured. The dental surface was either enamel, dentin or overdried dentin. Prior to the application of the adhesive composition, the dental surface was etched with a conventional phosphoric acid gel.

A commercially available light curing composite (Spectrum TPH, shade 2, Dentsply) was applied to the light cured surface of the adhesive.

The shear bond strength was measured. The results were compared to the shear bond strength available by using commercially available adhesive composition XP Bond, Prime & Bond NT. The results are shown in FIG. 1

Example 3

Indirect Restoration

The composition according to Example 1 was applied to a dental surface and light cured. The dental surface was either enamel or dentin. Prior to the application of the adhesive composition, the dental surface was etched with a conventional phosphoric acid gel.

A commercially available self curing composite (Calibra) was applied to the light cured surface of the adhesive.

Figure 2:
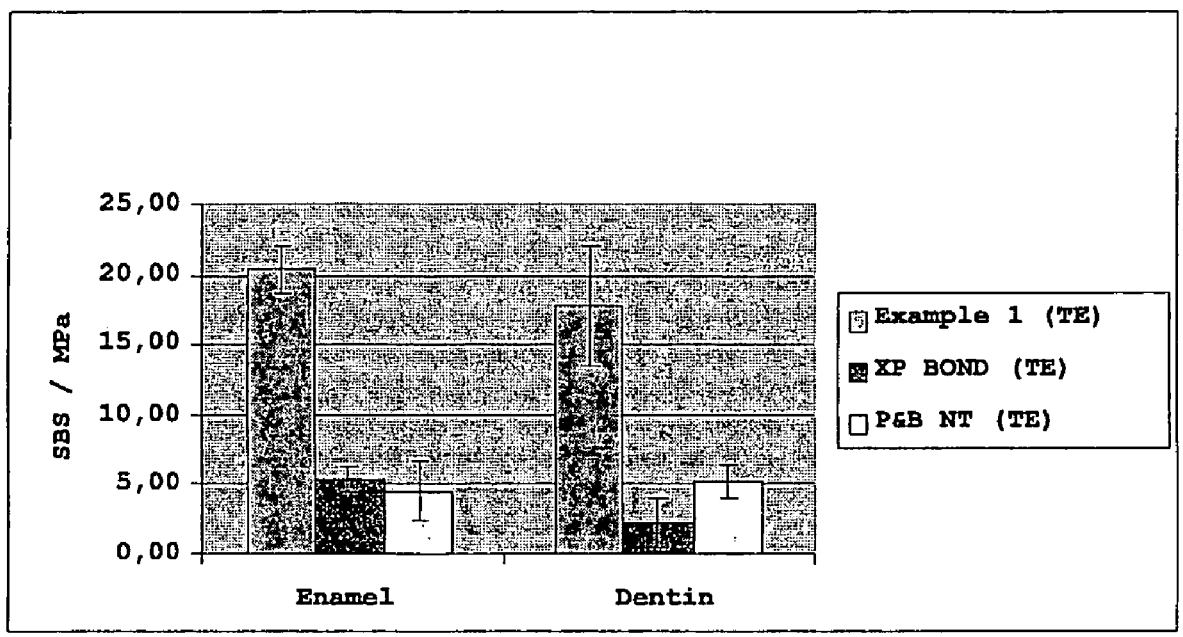
FIG. 2 shows the adhesion between a composition according to Example 1 and a self-curing composite cement (Calibra) in a total etch technique while light curing the adhesive layer and self-curing the composite cement after 24 h/37° C., as compared to XP Bond and Prime&Bond NT in total etch technique.

The shear bond strength was measured. The results were compared to the shear bond strength available by using commercially available adhesive composition XP Bond, Prime & Bond NT. The results are shown in FIG. 2.

A mixture of the composition of Example 1 and Prime&Bond self-cure activator was applied to a dental surface and self-cured. The dental surface was enamel or dentin. Prior to the application of the adhesive composition, the dental surface was etched with a conventional phosphoric acid gel.

A commercially available self curing composite (Calibra) was applied to the self-cured surface of the adhesive layer.

Figure 3:
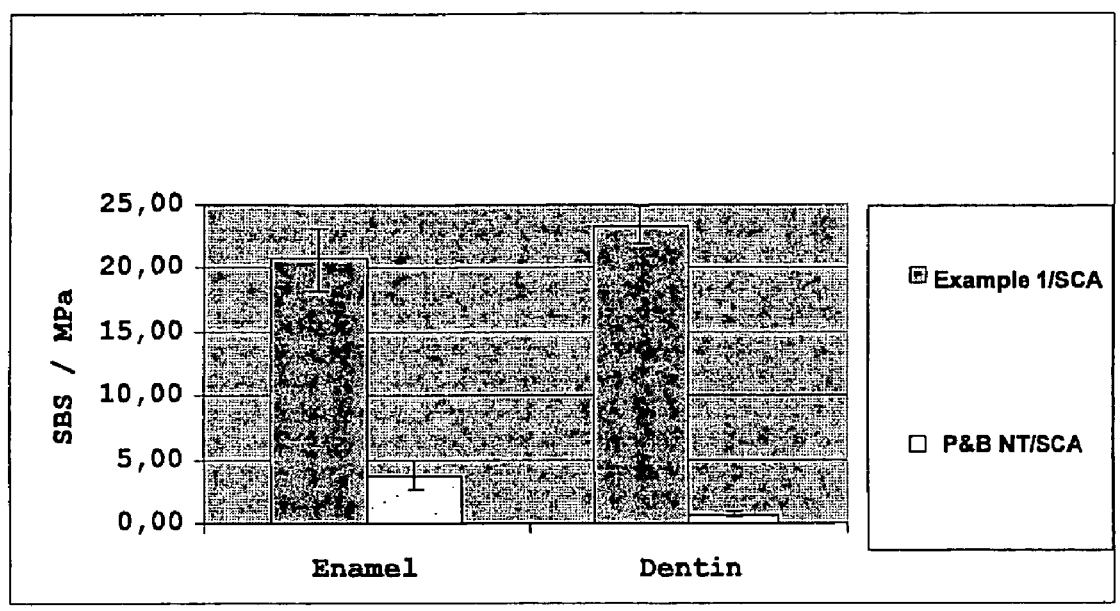
FIG. 3 shows the adhesion between a mixture, comprising of a composition, according to Example 1 and a commercial self-cure activator (Prime&Bond Self-cure Activator), and a self-curing composite cement (Calibra) in a total etch technique while self-curing the adhesive layer and self-curing the composite cement after 24 h/37° C., as compared to XP Bond and Prime&Bond NT in total etch technique.

The shear bond strength was measured. The results were compared to the shear bond strength available by using commercially available adhesive compositions XP Bond, Prime & Bond NT. The results are shown in FIG. 3.

The invention claimed is:

1. Dental adhesive composition having a pH of at least 5, consisting essentially of an aqueous solution containing
   (a) 20 to 60 wt % a plurality of different polymerizable N-substituted alkyl acrylic or acrylic acid amide monomers;
   (b) 3 to 20 wt % a water-soluble polymerizable carboxylic acid;
   (c) 5 to 45 wt % a water-soluble organic solvent; and
   (d) 5 to 45 wt % water; and
   optionally a filler, fluoride containing compound, initiator, stabilizer and/or inhibitor;
   wherein each of the plurality of different polymerizable N-substituted alkyl acrylic or acrylic acid amide monomers is characterized by one of the following formulas:

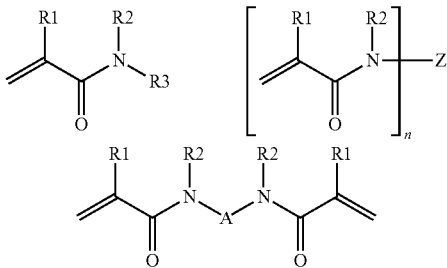

wherein
$R_1$ and $R_2$ independently represent a hydrogen atom or a $C_1$ to $C_8$ alkyl group,
A represents a divalent substituted or unsubstituted organic residue having from 1 to 11 carbon atoms, whereby said organic residue may contain from 1 to 3 oxygen and/or nitrogen atoms,
Z represents a saturated at least trivalent, substituted or unsubstituted $C_1$ to $C_8$ hydrocarbon group, a saturated at least trivalent substituted or unsubstituted cyclic $C_3$ to $C_8$ hydrocarbon group, and
n is at least 3.

2. The dental adhesive composition of claim 1, wherein the water-soluble polymerizable carboxylic acid is selected from the group of mono- or polycarboxylic acids.

3. The dental adhesive composition according to claim 2, wherein the water-soluble polymerizable carboxylic acid is present in an amount of from 5 to 15wt %.

4. The dental adhesive composition of claim 2, wherein the mono- or polycarboxylic acids are selected from the group of acrylic acid, methacrylic acid, fumaric acid, maleic acid, citric acid, itaconic acid, formic acid and mixtures thereof.

5. The dental adhesive composition according to claim 4, wherein the water-soluble organic solvent is selected from alcohols and ketones.

6. The dental adhesive composition according to claim 5, wherein the water-soluble organic solvent is selected from ethanol, n-propanol, i-propanol, n-butanol, t-butanol, acetone, and methyl ethyl ketone.

7. The dental adhesive composition according to claim 5, wherein the water-soluble organic solvent, is present in an amount of from 8 to 30 wt %.

8. The dental adhesive composition according to claim 1, wherein the water is present in an amount of from 20 to 40 wt %.

9. The dental adhesive composition according to claim 1, wherein components (a) and (b) are contained in a ratio of from 7:1 to 1:1 by weight.

10. The dental adhesive composition according to claim 9, wherein each of the plurality of different polymerizable N-substituted alkyl acrylic or acrylic acid amide monomer has a molecular weight of at most 400 g/mol.

11. The dental adhesive composition according to claim 10, wherein said water-soluble polymerizable carboxylic acid has a molecular weight of at most 400 g/mol.

12. The dental adhesive composition according to claim 1, wherein each of the plurality of different polymerizable N-substituted alkyl acrylic or acrylic acid amide monomers is a poly(meth) acrylamide characterized by the following formula:

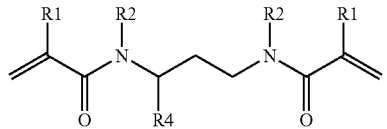

wherein
$R_1$, $R_2$ and $R_4$ independently represent
a hydrogen atom or
a $C_1$ to $C_8$ alkyl group.

13. The dental adhesive composition according to claim 12, which further consists essentially of a polymerization initiator, inhibitor and/or stabilizer.

14. The dental adhesive composition according to claim 13, wherein said polymerization initiator is a thermal initiator, a redox-initiator or a photo initiator.

15. The dental adhesive composition according to claim 14, wherein said photo initiator is acylphosphine oxide and/or camphor quinone/amine.

16. The dental adhesive composition according to claim 12, further consisting essentially of a nanofiller.

17. The dental adhesive composition according to claims 12, further comprising a fluoride compound.

18. The dental adhesive composition according to claim 12, wherein:
   (i) the water-soluble polymerizable carboxylic acid is selected from the group of mono- or polycarboxylic acids, the mono- or polycarboxylic acids are selected from the group of acrylic acid, methacrylic acid, fumaric acid, maleic acid, citric acid, itaconic acid, formic acid and mixtures thereof;
   (ii) the water-soluble organic solvent is selected from ethanol, n-propanol, i-propanol, n-butanol, t-butanol, acetone, and methyl ethyl ketone;

(iii) components (a) and (b) are present in a ratio of from 7:1 to 1:1 by weight; and (iv) the water being present in an amount of from 20 to 40 wt %.

19. The dental adhesive composition according to claim 12, wherein the dental adhesive composition provides adhesion in terms of shear bond strength to dentin and enamel at a level of at least 15 MPa, whereby the adhesion to dentin in terms of the shear bond strength is at least 50% of the adhesion to enamel in terms of the shear bond strength.

20. The dental adhesive composition according to claim 1, wherein:
(i) the water-soluble polymerizable carboxylic acid is selected from the group of mono- or polycarboxylic acids, the mono- or polycarboxylic acids are selected from the group of acrylic acid, methacrylic acid, fumaric acid, maleic acid, citric acid, itaconic acid, formic acid and mixtures thereof;
(ii) the water-soluble organic solvent is selected from ethanol, n-propanol, i-propanol, n-butanol, t-butanol, acetone, and methyl ethyl ketone;

(iii) components (a) and (b) are present in a ratio of from 7:1 to 1:1 by weight; and (iv) the water being present in an amount of from 20 to 40 wt %.

21. The dental adhesive composition according to claim 20, further consisting essentially of a nanofiller, a fluoride compound, or both.

22. The dental adhesive composition according to claim 1, wherein the dental adhesive composition provides adhesion in terms of shear bond strength to dentin and enamel at a level of at least 15 MPa, whereby the adhesion to dentin in terms of the shear bond strength is at least 50% of the adhesion to enamel in terms of the shear bond strength.

23. The dental adhesive composition according to claim 1, wherein the plurality of different polymerizable N-substituted alkyl acrylic or acrylic acid amide monomers includes 1,3-Bisacrylamido propane, 1,3-Bisacrylamido pentane, or both 1,3-Bisacrylamido propane and 1,3-Bisacrylamido pentane.

* * * * *